Figure 1:
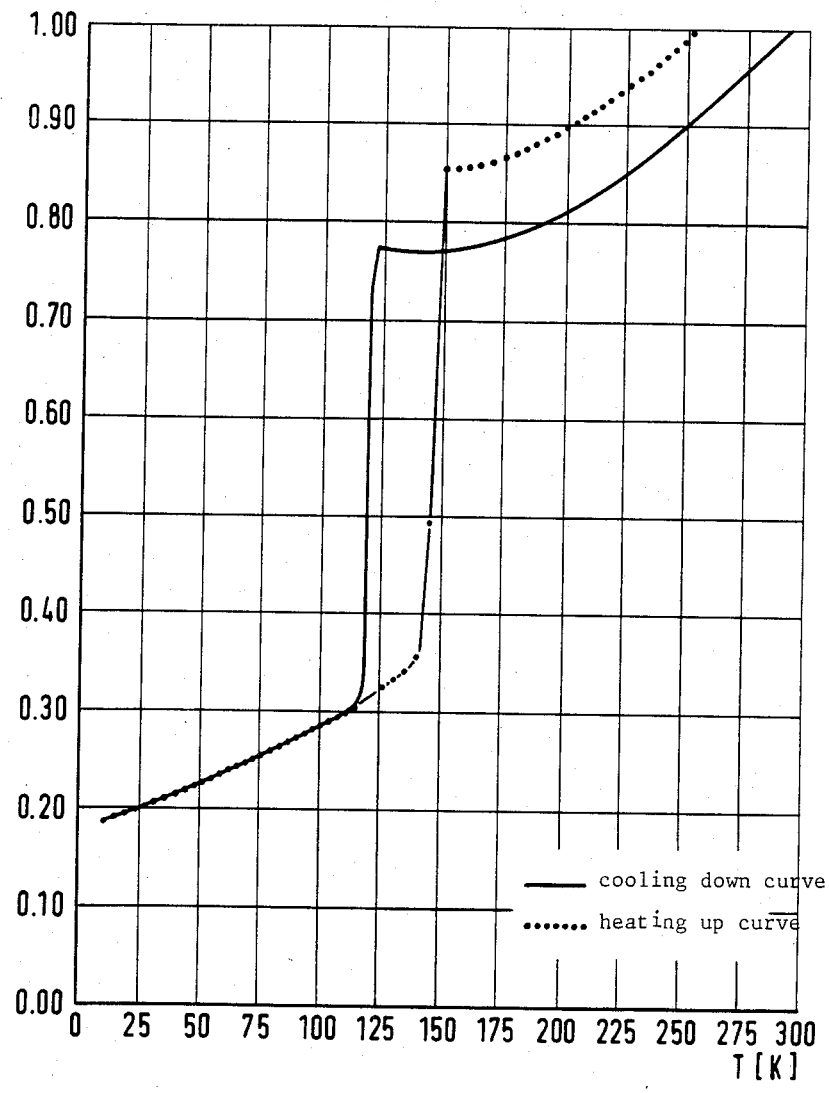

United States Patent [19]

Hilti et al.

[11] Patent Number: 4,601,853
[45] Date of Patent: Jul. 22, 1986

[54] (2-FLUORO-5,6,11,12-TETRASELENOTETRACENE)$_2$ CHLORIDE

[75] Inventors: Bruno Hilti, Basel; Carl W. Mayer, Riehen, both of Switzerland

[73] Assignee: Ciba-Geigy Corporation, Ardsley, N.Y.

[21] Appl. No.: 697,995

[22] Filed: Feb. 4, 1985

[30] Foreign Application Priority Data

Feb. 13, 1984 [CH] Switzerland .................. 678/84

[51] Int. Cl.$^4$ ............... C07D 517/06; H01B 1/00; B32B 9/04
[52] U.S. Cl. ............ 260/239 R; 204/157.97; 260/694; 252/500; 361/433; 562/460; 568/326; 570/183; 428/411
[58] Field of Search .................. 260/239 R

[56] References Cited

U.S. PATENT DOCUMENTS

| | | | |
|---|---|---|---|
| 3,769,276 | 10/1973 | Klingsberg | 260/239 R |
| 3,984,593 | 10/1976 | Hilti et al. | 260/239 R |
| 4,384,025 | 5/1983 | Hilti et al. | 260/239 R |
| 4,496,638 | 1/1985 | Sugiuchi et al. | 260/239 R |
| 4,522,754 | 6/1985 | Hilti et al. | 260/239 R |

FOREIGN PATENT DOCUMENTS

| | | |
|---|---|---|
| 23988 | 2/1981 | European Pat. Off. |
| 109360 | 5/1984 | European Pat. Off. |
| 899561 | 1/1982 | U.S.S.R. ............ 260/239 R |

OTHER PUBLICATIONS

AS USSR Chem. Phys., SU-899561, Derwent Abst.

Primary Examiner—Donald G. Daus
Assistant Examiner—Cecilia Shen
Attorney, Agent, or Firm—Michael W. Glynn; Irving M. Fishman

[57] ABSTRACT

The novel complex of the formula I

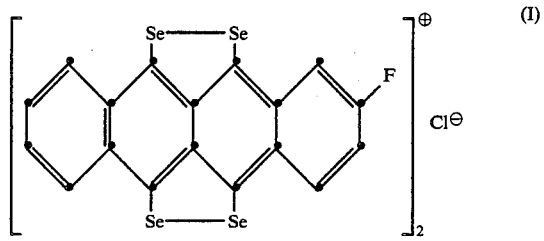

is an organic material with a high electrical conductivity and with a metallic phase transition at about 125° K. under normal pressure, at which the conductivity increases suddenly. The complex can be used, for example, as an organic electrical conductor.

1 Claim, 1 Drawing Figure

SPECIFIC ELECTRICAL RESISTANCE OF $(FTSeT)_2Cl$ AS A FUNCTION OF THE TEMPERATURE, STANDARDISED TO 295 K

(2-FLUORO-5,6,11,12-TETRASELENOTETRACENE)₂ CHLORIDE

The invention relates to (2-fluoro-5,6,11,12-tetraselenotetracene)₂ chloride, a process for its preparation and its use in information systems or electronic components.

Various mechanically conductive chalcogenated tetracene complexes, for example (5,6,11,12-tetraselenotetracene)₂ iodine, bromide or chloride or (5,6,11,12-tetrathiotetracene)₂(idodine)₃, are known from the literature. These complexes exhibit a relatively sharp transition from the metallic to the non-conductive state at temperatures between about 30 and 45 K, i.e. the metallic phase of these complexes is not stable down to sufficiently low temperatures at which, for example, superconductivity can be expected. It is also known that the transition point from the metallic to the non-conductive state in the (tetrathiotetracene)₂(iodine)₃ complex can be reduced under pressure or by changing the stoichiometry (increasing the iodine concentration above the 2:3 ratio). It is assumed that the stabilisation of the metallic phase in complexes which deviate from the exact 2:3 stoichiometry is caused by a change in the occupation of the bands. The mechanism which causes the stabilisation of the metallic phase of the above complexes under the influence of pressure is still largely unknown. No complexes based on 5,6,11,12-tetrathiotetracene or -tetraselenotetracene halides which exhibit a metallic phase transition only as a result of a change in temperature and without the influence of pressure have yet been disclosed.

The present invention relates to a complex of the formula I

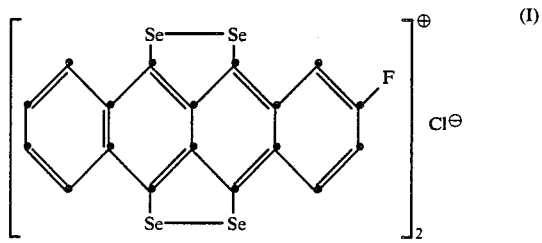

which, surprisingly and in contrast, for example, to the abovementioned (tetraselenotetracene)₂-iodine, -bromine or -chloride complexes, is distinguished by a stable metallic phase down to at least 5 K under normal pressure, i.e. the electrical conductivity of the complex increases from room temperature (20°-25° C.) down to at least 5° K. Moreover, a marked jump in the increase in the conductivity is observed at about 125 K. The complex of the formula I exhibits an electrical conductivity [$\sigma$] of up to 1,200 ohm$^{-1}$ cm$^{-1}$ at room temperature and an electrical conductivity of 7,000 ohm$^{-1}$ cm$^{-1}$ at 5 K (measured around the preferred direction of growth=axis of the needle). At 125 K, the conductivity increases suddenly by a factor of 2.6.

The complex according to the invention contains the space group P$_{2/n}$. The length of the axes of the unit cells are: a=1.7492 nm, b=0.5159 nm and c=1.7486 nm. The complex is monoclinical and, in addition to the high electrical conductivity, also has a pronounced electrical and optical anisotropy.

The complex according to the invention can be, for example, in the form of microcrystalline powders, as an amorphous layer, as a layer of microcrystals, as an amorphous powder or in the form of monocrystals, and can be used as an electrical conductor.

FIG. 1 shows a projection of the crystal structure of the complex according to the invention.

The complex of the formula I can be prepared by various methods, for example by (direct) oxidation of 2-fluoro-5,6,11,12-tetraselenotetracene with chlorine or an oxidising chlorine salt which splits off chlorine, such as copper(II) chloride and FeCl₃, in the presence of an inert organic solvent. Examples of suitable inert organic solvents are halogenated aliphatic hydrocarbons, such as methylene chloride and 1,1,2-trichloroethane; polar substituted, in particular halogenated, aromatic hydrocarbons, such as chlorobenzene, o-dichlorobenzene, 1,2,3-trichlorobenzene, 1,2,4-trichlorobenzene and chlorinated maphthalenes; other polar solvents, such as benzonitrile and alkylnitriles with 2-5 C atoms, for example acetonitrile, propionitrile and butyronitrile; nitrobenzene; N,N-dialkylamides of aliphatic monocarboxylic acids with 1-4 C atoms in the acid part, for example N,N-dimethylformamide and N,N-dimethylacetamide; N,N,N',N'-tetramethylurea; dialkylsulfoxides, such as dimethylsulfoxide and diethylsulfoxide; and cyclic ethers, such as tetrahydropyran, tetrahydrofuran and dioxane. Mixtures of the solvents mentioned can also be used. The reaction temperatures in these oxidation reactions are in general between 20° and 120° C.

The complex of the formula I can also be prepared by diffusion of chlorine from the gas phase or from a carrier solution into a solution of 2-fluoro-5,6,11,12-tetraselenotetracene, possible solvents being those of the abovementioned type.

The complex of the formula I can furthermore be prepared from the gas phase, i.e. by cosublimation of 2-fluoro-5,6,11,12-tetraselenotracene and chlorine by a process analogous to that described in German Patent Specification No. 2,641,742. In this process, the 2-fluoro-5,6,11,12-tetraselenotetracene and the chlorine are advantageously allowed to react with one another in an inert gas atmosphere, preferably in an open system. However, the reaction in the gas phase can also be carried out in a closed system in an inert gas atmosphere. The reaction in the gas phase can be carried out, for example, by bringing chlorine gas into contact with 2-fluoro-5,6,11,12-tetraselenotetracene by means of an inert carrier gas in the gas phase at about 260° C. In this procedure, the crystals grow in the desired form, for example in the form of rods or tubes, on the reactor walls and/or any substrate which may be located in the reactor, such as aluminium oxide or, preferably, quartz. The carrier gases which are used in this preparation method are advantageously highly pure inert gases, such as argon, nitrogen, helium and xenon. The reaction temperatures in the gas phase reaction are advantageously between 180° and 300° C. The crystals obtained by a gas phase reaction can easily be removed from the reaction chamber or from the substrate. A suitable experimental design for this preparation method is described in the abovementioned German Patent Specification No. 2,641,742.

Preferably, however, the complex according to the invention is prepared by electrochemical oxidation of 2-fluoro-5,6,11,12-tetraselenotetracene in the presence of an inert organic solvent and a chloride-containing conductive salt. Inert organic solvents which can be used are those of the abovementioned type. Preferred solvents are cyclic ethers and N,N-dialkylamides of aliphatic monocarboxylic acids or mixtures thereof, in particular tetrahydrofuran and N,N-dimethylformamide or mixtures thereof. Examples of suitable chloride-containing conductive salts are salts of the formula II

in which Y is N, P or As and $R_1$ to $R_4$ independently of one another are $C_{1-18}$-alkyl, benzyl, phenyl or naphthyl. Alkyl groups $R_1$ to $R_4$ can be straight-chain or branched and preferably contain 1-12 C atoms. Examples of such alkyl groups are: methyl, ethyl, n-propyl, isopropyl, n-butyl, sec.-butyl, tert.-butyl, 1,1,3,3-tetramethylbutyl, n-pentyl, 2-pentyl, n-hexyl, n-heptyl, n-octyl, n-decyl, n-dodecyl, n-tetradecyl, n-hexadecyl and n-octadecyl. Compounds of the formula II in which Y is N or P, $R_1$ is benzyl or phenyl and $R_2$ to $R_4$ are straight-chain alkyl with in each case 1-12 C atoms or phenyl, or $R_1$ and $R_4$ are straight-chain alkyl with in each case 1-12 C atoms, are preferably used. Compounds of the formula II in which Y is N and $R_1$ to $R_4$ are straight-chain alkyl with in each case 1-12 C atoms, and in particular in each case n-hexyl, are particularly preferred.

Between 0.01 and 30 g of conductive salt per liter are advantageously used, depending on the temperature of the electrolysis cell and the solvent employed. Devices which are known per se can be used as the electrolysis cells, for example those in which the anode chamber is separated from the cathode chamber by a Teflon screen, glass frits or capillaries. The dimensions of the electrolysis cells can vary depending on the amount of reaction components used, and have virtually no adverse effect on the quality of the resulting complex of the formula I. Cell volumes of, for example, 15–100 ml are particularly suitable for the preparation of about 5–50 mg of complex of the formula I.

The reaction temperatures (temperatures of the electrolysis cells) are advantageously between 0° and 120° C., depending on the nature of the solvent used. The current strength in general varies between 0.005 μA and 5 μA. The diameter of the anodes and cathodes is advantageously between 0.1 and 5 mm.

In the above reactions, at least stoichiometric amounts of the 2-fluoro-5,6,11,12-tetraselenotetracene and chlorine or chloride salt are employed. However, it is generally advisable to start with an excess of chlorine or chloride salt, so that there is a 20-fold to 1,000-fold molar excess of chlorine or chloride salt in the reaction phase at any time.

2-(Fluoro)-5,6,11,12-tetraselenotetracene (formula VI) can be obtained via the intermediates of the formulae III to V

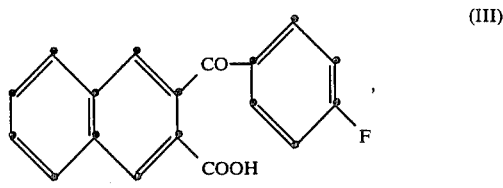

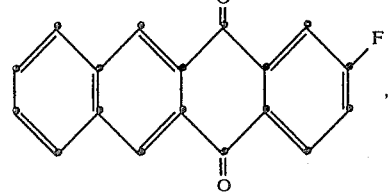

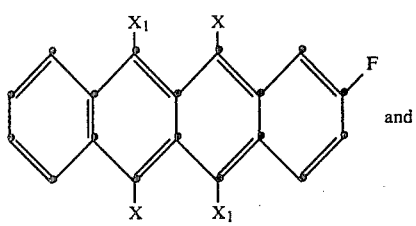

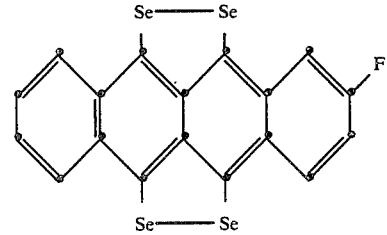

in which the symbols $X_1$ and X are each hydrogen or the symbols $X_1$ are each hydrogen and the symbols X are each chlorine or the symbols $X_1$ are each chlorine and the symbols X are each hydrogen.

The compounds of the formulae III to VI can be prepared by processes which are analogous to those which are known per se, by reacting 2,3-naphthalenedicarboxylic anhydride with fluorobenzene in the presence of a Friedel Crafts catalyst, preferably aluminium chloride, to give the compound of the formula III, cyclising the 2-(4-fluorobenzoyl)-naphthalene-3-carboxylic acid to give 2-fluoro-5,12-naphthacene-quinone (compound of the formula IV), reducing the compound of the formula IV to give 2-fluorotetracene (compound of the formula V where $X_1$ and X=H), for example in the presence of zinc dust in an acid medium, for example acetic acid, reacting the 2-fluorotetracene with sulfuryl chloride to give 2-fluoro-5,11- or 2-fluoro-6,12-dichlorotetracene [c.f., for example, Bull. Soc. Chim. France, 427 (1948)], and, finally, reacting the 2-fluoro-5,11- or 2-fluoro-6,12-dichlorotetracene or a mixture thereof with selenium at elevated temperature.

The cyclisation of the 2-(3-fluorobenzoyl)-naphthalene-3-carboxylic acid to give 2-fluoro-5,12-naphthacene-quinone can be carried out in a manner which is known per se in the presence of a proton acid or a Lewis acid. Examples of suitable proton acids are polyphosphoric acid, chlorosulfonic acid and sulfuric acid. Examples of possible Lewis acids are boron trifluoride and, in particular, aluminium trichloride. Cyclisation in the presence of a Lewis acid, in particular aluminium chloride, in the melt is preferred. The reaction of the 5-fluorotetracene with sulfuryl chloride and the reaction of the 2-fluoro-5,11- or 2-fluoro-6,12-dichlorotetracene with selenium are advantageously carried out in the presence of an inert organic solvent. Suitable solvents for the reaction of the 2-fluorotetracene with sulfuryl chloride are, for example, nitrobenzene, benzene and carbon tetrachloride. Nitrobenzene is the preferred solvent.

The reaction of the 2-fluoro-5,11- or 2-fluoro-6,12-dichlorotetracene is preferably carried out in the presence of a halogenated aromatic hydrocarbon, in particular 1,2,4-trichlorobenzene.

On the basis of the mechanically electrical conductivity and the marked electrical and optical anisotropy, the complex according to the invention is suitable for use as an organic electrical conductor, for example for conductive coatings on plastic fibres; and furthermore as a polariser material or as an additive to antistatic coatings and coverings, for example those based on plastic. The complex of the formula I can also be employed in highly conductive printing materials or processes which are sensitive towards electron beams or are photosensitive, such as those described, for example, in European Patent Application Publication No. 23,988 and U.S. Pat. Spec. No. 4,036,648. Due to its redox properties and the carious intensive colours of its redox stages (green, blue-green, blue and yellow), the complex of the formula I can furthermore be advantageously used in information systems, such as colour display screens, and in electronic components. The highly conductive complex of the formula I is particularly suitable for this purpose, since it can be subjected to further oxidation and reduction in electrical arrangements, such as, for example, electrochromic circuits. However, on the basis of its metallic phase, which is stable down to about 5 K, the complex according to the invention is particularly suitable for various uses in low temperature technology, for example for use as an electrically conductive layer in capacitor films or as cathode material in solid electrolyte cells, which can thus also be used at a low temperature. The complex can furthermore be used for pressure- and/or temperature-dependent circuit elements or for circuit elements which depend on a magnetic field.

EXAMPLE (a) 45.0 g (227 mmol) of 2,3-naphthalenedicarboxylic acid anhydride are suspended in 200 ml (2.1 moles) of fluorobenzene. 75.5 g (565 mmol) of powdered aluminium chloride are added in the course of 5 minutes, with vigorous stirring (exothermic reaction up to about 32° C.). The dark red suspension is refluxed and stirred for 6 hours. The solution is then allowed to cool to room temperature and is poured onto about 500 g of ice, and is stirred to bring the hydrolysis to completion. Excess fluorobenzene is evaporated off and the resulting product is suspended in water. The suspension is filtered, the filtrate is rinsed with water and the product is dried. 76 g of crude 2-(4-fluorobenzoyl)-naphthalene-3-carboxylic acid are obtained. The crude product is stirred with 2 liters of 10% sodium carbonate solution, the resulting solution is acidified with hydrochloric acid and the white precipitate is filtered off and dried. 54.2 g (81% of theory) of 2-(4-fluorobenzoyl)-naphthalene-3-carboxylic acid are obtained.

Mass spectrum: ($M^+$=294; $M^+$—COOH=249, $M^+$—COO=250, $M^+$—$C_6H_4F$=199);

IR spectrum (KBr): OH about 3,300 cm$^{-1}$; C=O double band 1,695/1,705 cm$^{-1}$.

(b) 200 g (1.5 moles) of powdered aluminium chloride and 40 g (684 mmol) of sodium chloride are heated together at 140°–150° C. After about 1.5 hours, 40 g (136 mmol) of 2-(4-fluorobenzoyl)-naphthalene-3-carboxylic acid are added to the melt. The dark red mixture is stirred at 140°–150° C. for one hour. Hydrolysis is then carried out at about 100° C. by slowly adding ice-water. The precipitate is filtered off and stirred with 10% sodium carbonate solution. It is then washed neutral with water and dried. The resulting product is sublimed at 230° C. 13.1 g (70% of theory) of 2-fluoro-5,12-naphthacenequinone are obtained.

Thin layer chromatography: silica gel, benzene: $R_x \simeq 0.6$; yellow fluorescent spot.

NMR (100 MHz in $CDCL_3$): multiplet which is complicated but can be interpreted, in the aromatic region.

Mass spectrum: $M^+$=276, $M^+$—CO=248, $M^+$—2-CO=220.

(c) 8.0 g (29 mmol) of 2-fluoro-5,12-naphthacenequinone, 40 ml of water, 680 ml of acetic acid and 40 g (611 mmol) of zinc dust are brought together and refluxed. After refluxing for 30 minutes, with stirring, the mixture is cooled and 200 ml of water are added. The resulting suspension of 2-fluorotetracene is decanted off, the zinc dust remaining in the flask. The 2-fluorotetracene is filtered off, washed with water and ethanol and dried. After recrystallisation from 500 ml of xylene, 4.0 g (56% of theory) of 2-fluorotetracene are obtained.

UV (benzene): typical tetracene spectrum. $\lambda_{max}$ 476, 446, 420 and 394 nm.

Mass spectrum: $M^+$=246, $M^{+2}$=123.

(d) 5.0 g (20.3 mmol) of 2-fluorotetracene are suspended in 25 ml of nitrobenzene, under nitrogen, and the suspension is cooled to 5° C. 5.9 g (43.7 mmol) of sulfuryl chloride in 25 ml of nitrobenzene are then added dropwise in the course of 30 minutes and the mixture is stirred at 5° C. for 2 hours. The temperature is then allowed to rise to 20°–25° C. and the mixture is heated to 90° C. in the course of 1.5 hours, stirred at this temperature for 10 minutes and cooled. The suspension is filtered off, rinsed with about 600 ml of ethanol and dried. 5.0 g (78% of theory) of 2-fluoro-5,11- or 6,12-dichlorotetracene are obtained. Mass spectrum: $M^+$=314/316 (=2 Cl), $M^+$—HCl=278, $M^+$—2Cl=244, $M^{+2}$=157/158 (2 Cl).

(e) 7.2 g (22.8 mmol) of 2-fluoro-5,11-dichlorotetracene, 7.7 g (97.5 mmol) of selenium and 175 ml of trichlorobenzene are brought together and are refluxed at a bath temperature of 250° C. under nitrogen for 120 hours. After 70 hours, a further 3.8 g (48.1 mmol) of selenium are added. The suspension is then allowed to cool and is diluted with about 200 ml of n-hexane and filtered. The product is rinsed with benzene and n-hexane and dried, and is then sublimed under a high vacuum at 260°–270° C./$10^{-3}$ bar. 4.4 g (35% of theory) of 2-fluoro-5,6,11,12-tetraselenotetracene are obtained. UV spectrum in trichlorobenzene: $\lambda_{max}$=719, 659 and 466 nm.

(f) 30 mg of 2-fluoro-5,6,11,12-tetraselenotetracene are introduced into the anode chamber of an electrolysis cell with a volume of 40 ml. 60 mg of tetra-n-hexylammonium chloride are added as a conductive salt. The cell is evacuated under $5 \times 10^{-2}$ mbar overnight in a drying cabinet and is flushed with argon. 33 ml of a mixture of 25% by volume of chlorobenzene and 75% by volume of N,N-dimethylformamide are then added as the solvent. After the mixture has been heated up to 90° C. for 4 hours, the cell is placed under a voltage of 0.1 volt for 1 hour; this voltage is increased to 0.4 volt in 3 stages in the course of 2 days, an electrolysis current of 1.06 μA being established. After 8 days, the crystals formed at the anode (diameter 1 mm; 80% by weight of Pt, 20% by weight of IR) are detached by washing off with ethanol. Four crystals with average dimensions of 4 mm×40 μm×40 μm are mounted on 4 probes consisting of gold wires 25 μm thick by means of platinum paste (Pt paste 308 from Degussa). The conductivity of the crystals at room temperature, measured in the above probe arrangement, varies from 700 to 1,200 ohm$^{-1}$ cm$^{-1}$. The temperature-dependency of the specific resistance, standardised to 295 K, shows, for all the crystals, the behaviour shown in FIG. 1, within a measurement accuracy of 2%.

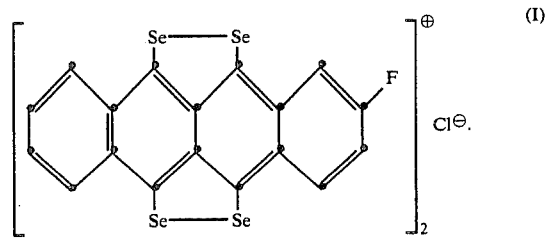

What is claimed is:
1. The complex of the formula I